(12) United States Patent
Palushi et al.

(10) Patent No.: US 11,419,623 B2
(45) Date of Patent: Aug. 23, 2022

(54) SINUPLASTY INSTRUMENT WITH MOVEABLE NAVIGATION SENSOR

(71) Applicant: Acclarent, Inc., Irvine, CA (US)

(72) Inventors: Jetmir Palushi, Irvine, CA (US); Henry F. Salazar, Pico Rivera, CA (US); Jordan R. Trott, Redondo Beach, CA (US)

(73) Assignee: Acclarent, Inc., Irvine, CA (US)

( * ) Notice: Subject to any disclaimer, the term of this patent is extended or adjusted under 35 U.S.C. 154(b) by 302 days.

(21) Appl. No.: 16/665,123

(22) Filed: Oct. 28, 2019

(65) Prior Publication Data

US 2020/0187967 A1 Jun. 18, 2020

Related U.S. Application Data

(60) Provisional application No. 62/778,341, filed on Dec. 12, 2018.

(51) Int. Cl.
*A61B 5/06* (2006.01)
*A61B 17/24* (2006.01)
(Continued)

(52) U.S. Cl.
CPC .............. *A61B 17/24* (2013.01); *A61B 5/065* (2013.01); *A61B 34/20* (2016.02); *A61M 25/09* (2013.01); *A61M 25/1018* (2013.01); *A61M 29/02* (2013.01); *A61B 2034/2051* (2016.02); *A61M 2025/09008* (2013.01); (Continued)

(58) Field of Classification Search
CPC .......... A61B 1/233; A61B 2017/00367; A61B 90/30; A61M 2025/09116; A61M 2025/09175; A61M 2025/09183; A61M 2210/0618; A61M 2210/0668; A61M 2210/0675; A61M 2210/0681;
(Continued)

(56) References Cited

U.S. PATENT DOCUMENTS 7,720,521 B2 5/2010 Chang et al.
10,561,370 B2 2/2020 Salazar et al.
(Continued)

OTHER PUBLICATIONS

International Search Report and Written Opinion dated Jun. 25, 2020 for International Application No. PCT/IB2019/060500, 19 pages.

*Primary Examiner* — Deanna K Hall
(74) *Attorney, Agent, or Firm* — Frost Brown Todd LLC

(57) ABSTRACT

An apparatus includes a handle assembly, a guide member extending distally from the handle assembly, and a dilation catheter slidably disposed relative to the guide member. The dilation catheter includes an expandable element configured to dilate a paranasal sinus ostium of a patient. A navigation sensor is movably disposed at the distal end of the guide member and is operable to generate a signal corresponding to a location thereof within the patient. The navigation sensor is configured to translate distally with the dilation catheter relative to the guide member when a distal end of the dilation catheter translates distally beyond the distal end of the guide member. The navigation sensor is further configured to assume a position at the distal end of the guide member when the distal end of the dilation catheter retracts proximally of the distal end of the guide member.

20 Claims, 12 Drawing Sheets

(51) Int. Cl.
 *A61B 34/20* (2016.01)
 *A61M 25/09* (2006.01)
 *A61M 29/02* (2006.01)
 *A61M 25/10* (2013.01)

(52) U.S. Cl.
 CPC .............. *A61M 2025/09116* (2013.01); *A61M 2029/025* (2013.01); *A61M 2210/0681* (2013.01)

(58) Field of Classification Search
 CPC ...... A61M 2210/1028; A61M 25/0136; A61M 2025/0175
 See application file for complete search history.

(56) References Cited

U.S. PATENT DOCUMENTS

| | | |
|---|---|---|
| 2006/0004286 A1 * | 1/2006 | Chang .................... A61B 90/16 600/435 |
| 2010/0274188 A1 | 10/2010 | Chang et al. |
| 2011/0004057 A1 | 1/2011 | Goldfarb et al. |
| 2012/0071857 A1 | 3/2012 | Goldfarb et al. |
| 2012/0078118 A1 | 3/2012 | Jenkins et al. |
| 2013/0274715 A1 | 10/2013 | Chan et al. |
| 2014/0074141 A1 | 3/2014 | Johnson et al. |
| 2014/0364725 A1 | 12/2014 | Makower |
| 2016/0008083 A1 | 1/2016 | Kesten et al. |
| 2016/0151614 A1 | 6/2016 | Ressemann et al. |
| 2017/0120020 A1 | 5/2017 | Lin et al. |
| 2017/0259048 A1 * | 9/2017 | Matlock ............. A61M 25/0113 |
| 2018/0117290 A1 | 5/2018 | Matlock et al. |
| 2018/0214216 A1 | 8/2018 | Sema et al. |

* cited by examiner

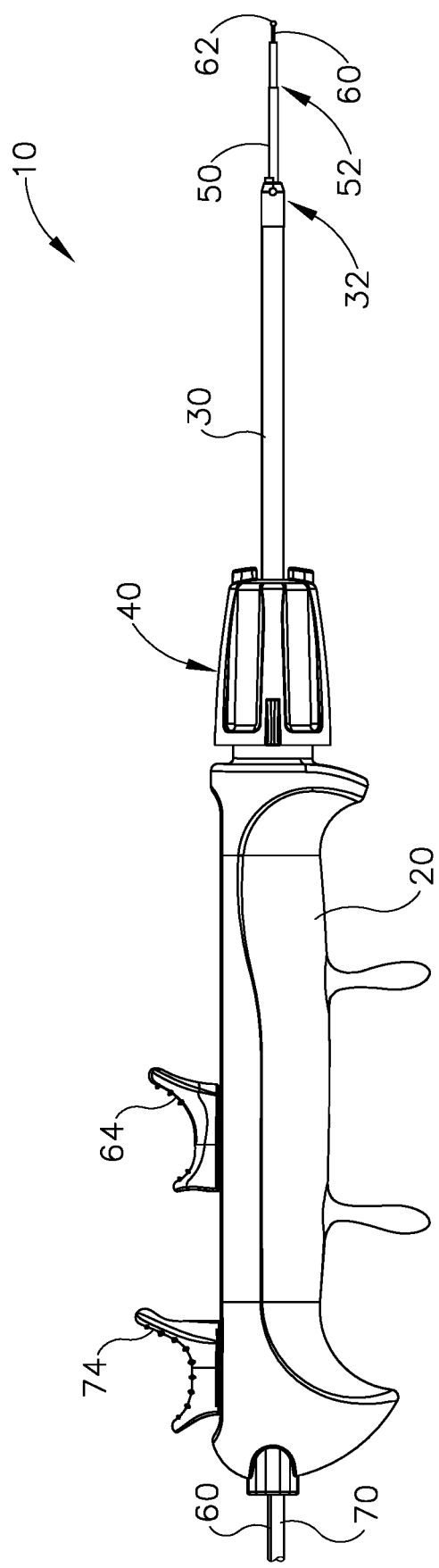

SINUPLASTY INSTRUMENT WITH MOVEABLE NAVIGATION SENSOR

PRIORITY

This application claims priority to U.S. Provisional Pat. App. No. 62/778,341, entitled "Sinuplasty Instrument with Moveable Navigation Sensor," filed Dec. 12, 2018, the disclosure of which is incorporated by reference herein in its entirety.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

In the context of Eustachian tube dilation, a dilation catheter or other dilation instrument may be inserted into the Eustachian tube and then be inflated or otherwise expanded to thereby dilate the Eustachian tube. The dilated Eustachian tube may provide improved ventilation from the nasopharynx to the middle ear and further provide improved drainage from the middle ear to the nasopharynx. Methods and devices for dilating the Eustachian tube are disclosed in U.S. Patent Pub. No. 2010/0274188, entitled "Method and System for Treating Target Tissue within the ET," published on Oct. 28, 2010, now abandoned, the disclosure of which is incorporated by reference herein; and U.S. Patent Pub. No. 2013/0274715, entitled "Method and System for Eustachian Tube Dilation," published on Oct. 17, 2013, now abandoned, the disclosure of which is incorporated by reference herein. An example of such a system is the Aera® Eustachian Tube Balloon Dilation System by Acclarent, Inc. of Irvine, Calif.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation systems that may be used in IGS procedures is the CARTO® 3 System by Biosense-Webster, Inc., of Irvine, Calif. In some IGS procedures, a digital tomographic scan (e.g., CT or MM, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

While several systems and methods have been made and used in surgical procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 1A depicts a side elevational view of an exemplary dilation instrument, in an initial configuration;

Figure 1B:
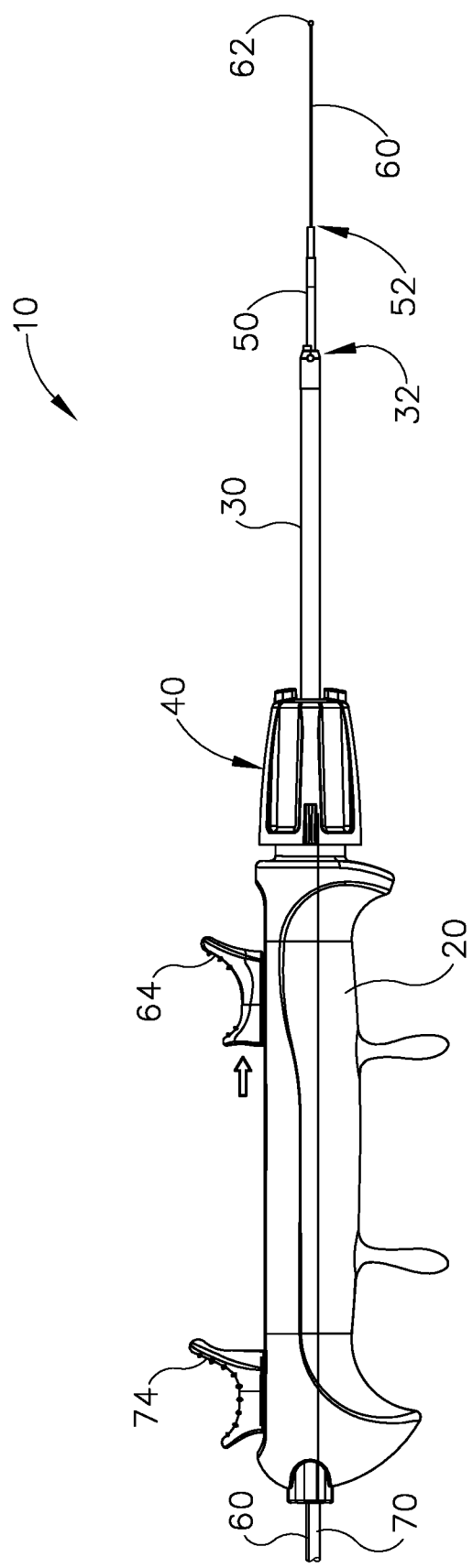
FIG. 1B depicts a side elevational view of the dilation instrument of FIG. 1A, with a guidewire advanced to a distal position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

As used herein, the terms "about" and "approximately" for any numerical values or ranges are intended to encompass the exact value(s) referenced as well as a suitable dimensional tolerance that allows the part or collection of components to function for its intended purpose as described herein.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Dilation Instrument

Figure 1C:
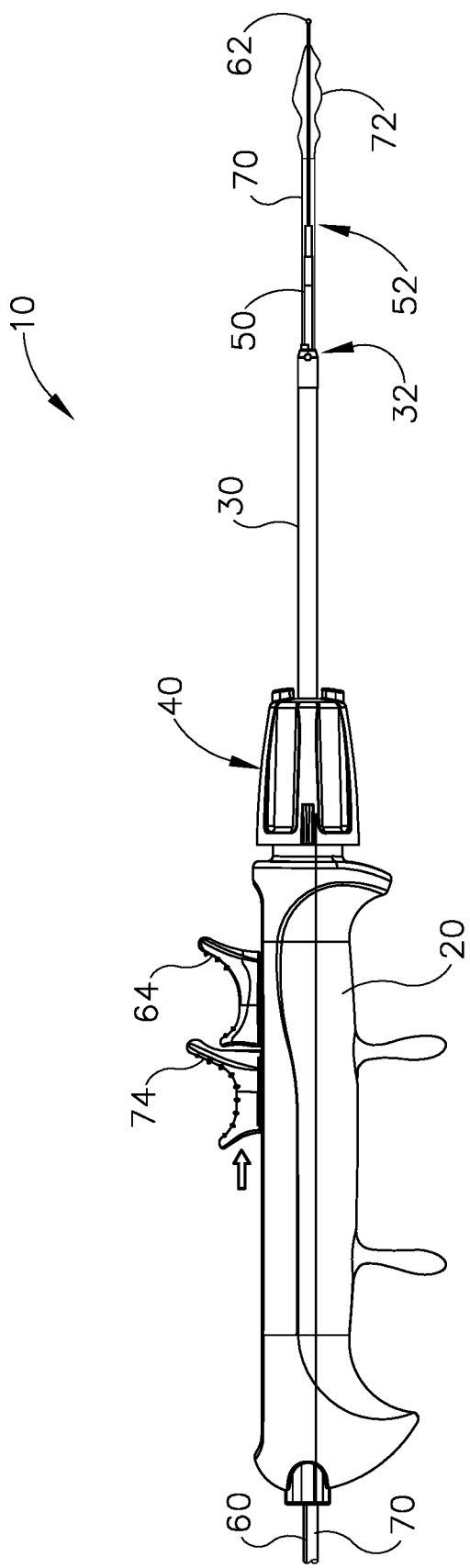
FIG. 1C depicts a side elevational view of the dilation instrument of FIG. 1A, with the guidewire advanced to the distal position of FIG. 1B, and with a dilation catheter advanced to a distal position.

FIGS. 1A-1C show an exemplary dilation instrument (10) that may be used to dilate the ostium of a paranasal sinus; or to dilate some other anatomical passageway (e.g., within the ear, nose, or throat, etc.). By way of example only, dilation instrument (10) may be configured and operable in accordance with at least some of the teachings of U.S. Pub. No. 2012/0071857, entitled "Methods and Apparatus for Treating Disorders of the Sinuses," published Mar. 22, 2012, now abandoned, the disclosure of which is incorporated by reference herein. In addition or in the alternative, dilation instrument (10) may be configured and operable like the Relieva Scout® Sinus Dilation System by Acclarent, Inc. of Irvine, Calif.

Dilation instrument (10) of the present example comprises a handle assembly (20), a rigid guide member (30), a rotary knob (40), a malleable guide member (50), a guidewire (60), and a dilation catheter (70). Rigid guide member (30) extends distally from handle assembly (20) and is substantially straight. In the present example, the longitudinal position and angular position of rigid guide member (30) is fixed relative to handle assembly (20).

Figure 2A:
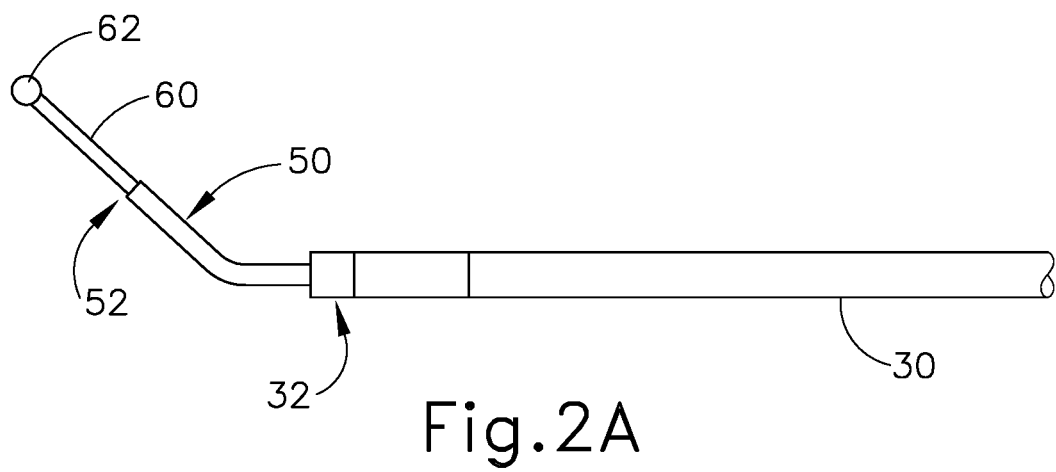
FIG. 2A depicts a side elevational view of the distal end of the dilation instrument of FIG. 1A, with a guide member of the instrument in a bent configuration, and with the guidewire advanced to the distal position.

Malleable guide member (50) protrudes distally from the open distal end (32) of rigid guide member (30). The outer diameter of malleable guide member (50) is smaller than the inner diameter of rigid guide member (30), such that a cylindraceous gap is defined between the outer diameter of malleable guide member (50) and the inner diameter of rigid guide member (30). This cylindraceous gap is sized to accommodate a translating dilation catheter (70) as will be described in greater detail below. While malleable guide member (50) is shown as having a straight configuration in FIGS. 1A-1C, malleable guide member (50) may be bent to various bend angles, for example as shown in FIG. 2A. Malleable guide member (50) is configured to substantially maintain a bend angle once bent, until the operator takes steps to intentionally unbend or re-bend malleable guide member (50). In other words, malleable guide member (50) has sufficient rigidity to maintain a selected bend angle during operation of dilation instrument (10) in a dilation procedure, such that use of dilation instrument (10) in a dilation procedure will not cause malleable guide member (50) to undesirably unbend or re-bend. In the present example, malleable guide member (50) is formed of metal, though any other suitable material(s) may be used.

Guidewire (60) is slidably received in a central lumen defined in malleable guide member (50). Guidewire (60) includes a rounded tip feature (62) that is located distal to the open distal end (52) of malleable guide member (50). Guidewire (60) is secured to a slider (64), which is slidably coupled with handle assembly (20). Slider (64) is thus operable to slide guidewire (60) between a proximal position (FIG. 1A) and a distal position (FIG. 1B). In the present example, tip feature (62) has an outer diameter that is larger than the inner diameter of distal end (52) of malleable guide member (50), such that tip feature (62) cannot be retracted proximally back through malleable guide member (50). In some versions, guidewire (60) includes one or more optical fibers, and tip feature (62) is configured to emit light communicated through such optical fibers. This may enable an operator to verify positioning of tip feature (62) within a sinus cavity through a transillumination effect as is known in the art. By way of example only, guidewire (60) may be configured and operable in accordance with at least some of the teachings of U.S. Pub. No. 2012/0078118, issued as U.S. Pat. No. 9,155,492 on Oct. 13, 2015, the disclosure of which is incorporated by reference herein. Other suitable forms that guidewire (60) may take will be apparent to those of ordinary skill in the art in view of the teachings herein.

Figure 2B:
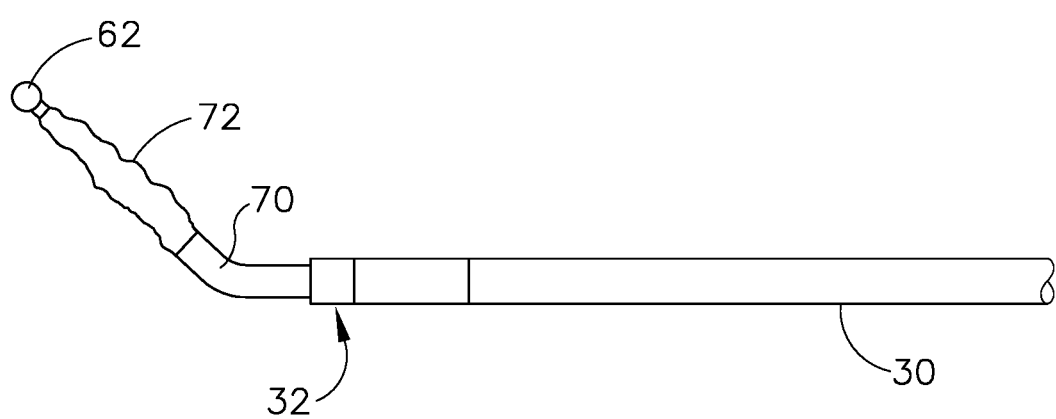
FIG. 2B depicts a side elevational view of the distal end of the dilation instrument of FIG. 1A, with the guide member of the instrument in the bent configuration of FIG. 2A, and with a dilation catheter advanced to a distal position.

Dilation catheter (70) is slidably disposed along malleable guide member (50) and is thus operable to translate through the cylindraceous gap defined between the outer diameter of malleable guide member (50) and the inner diameter of rigid guide member (30). Dilation catheter (70) is secured to a slider (74), which is slidably coupled with handle assembly (20). Slider (74) is thus operable to slide dilation catheter (70) between a proximal position (FIGS. 1B and 2A) and a distal position (FIGS. 1C and 2B). When dilation catheter (70) translates from the proximal position to the distal position, dilation catheter (70) passes over the open distal end (52) of malleable guide member (50) and then traverses along at least a portion of the length of guidewire (60) that extends distally from open distal end (52) of malleable guide member (50).

Figure 2C:
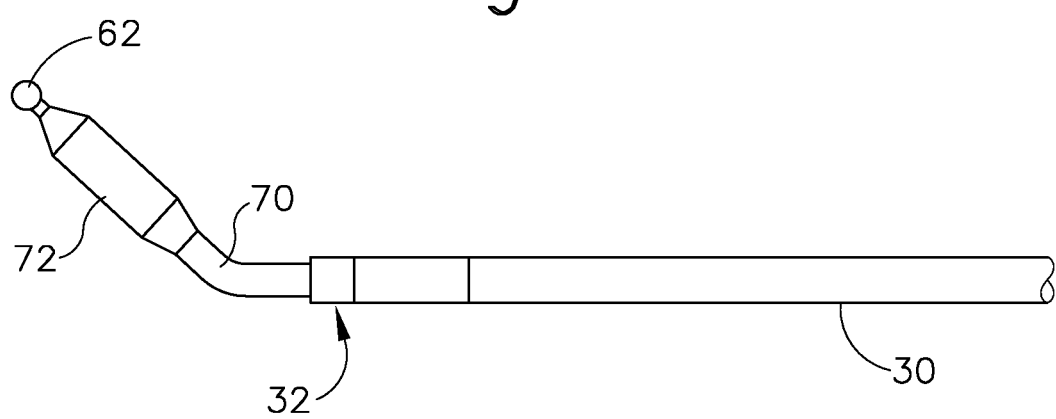
FIG. 2C depicts a side elevational view of the distal end of the dilation instrument of FIG. 1A, with the guide member of the instrument in the bent configuration of FIG. 2A, with the dilation catheter advanced to the distal position of FIG. 2B, and with a dilator of the dilation catheter in an expanded state.

The distal end of dilation catheter (70) comprises a dilator (72). Dilator (72) is operable to transition between a non-expanded state (FIG. 2B) and an expanded state (FIG. 2C). In the non-expanded state, dilator (72) may be inserted into a sinus ostium or other drainage passageway associated with a paranasal sinus. Dilator (72) may then be expanded to dilate the sinus ostium or other drainage passageway as described in various references herein. In the present example, dilator (72) comprises an inflatable balloon that receives saline (or some other fluid) for inflation, though it should be understood that dilator (72) may instead take a variety of other forms. In some versions, dilation catheter (70) is fluidly coupled with an inflator instrument that is constructed and operable in accordance with at least some of the teachings of U.S. Pub. No. 2014/0074141, entitled "Inflator for Dilation of Anatomical Passageway," published Mar. 13, 2014, issued as U.S. Pat. No. 9,962,530 on May 8, 2018, the disclosure of which is incorporated by reference herein.

Rotary knob (40) is fixedly secured to the proximal end of malleable guide member (50). Rotation of rotary knob (40) rotates malleable guide member (50), thereby re-orienting distal end (52) of malleable guide member (50) and tip feature (62) of guidewire (60). An operator may wish to provide such rotation and re-orientation based on the sinus in which guidewire (60) and dilation catheter (70) are to be inserted. In the present example, the angular position of rotary knob (40) and malleable guide member (50) is selectively locked or unlocked based on longitudinal positioning of rotary knob (40) relative to handle assembly (20). Thus, in order to rotate rotary knob (40) and malleable guide member (50) about the longitudinal axis of rigid guide member (30), the operator may grasp rotary knob (40), pull rotary knob (40) proximally, rotate rotary knob (40) to achieve a desired angular position while still pulling rotary knob (40) proximally, and then release rotary knob (40) to allow rotary knob (40) to return to the distal position.

Dilation instrument (10) may be further configured and operable in accordance with the teachings of U.S. Pub. No. 2017/0120020, entitled "Apparatus for Bending Malleable Guide of Surgical Instrument," published May 4, 2017, issued as U.S. Pat. No. 10,137,286 on Nov. 27, 2018, the disclosure of which is incorporated by reference herein.

II. Exemplary Image Guided Surgery Navigation System

Figure 3:
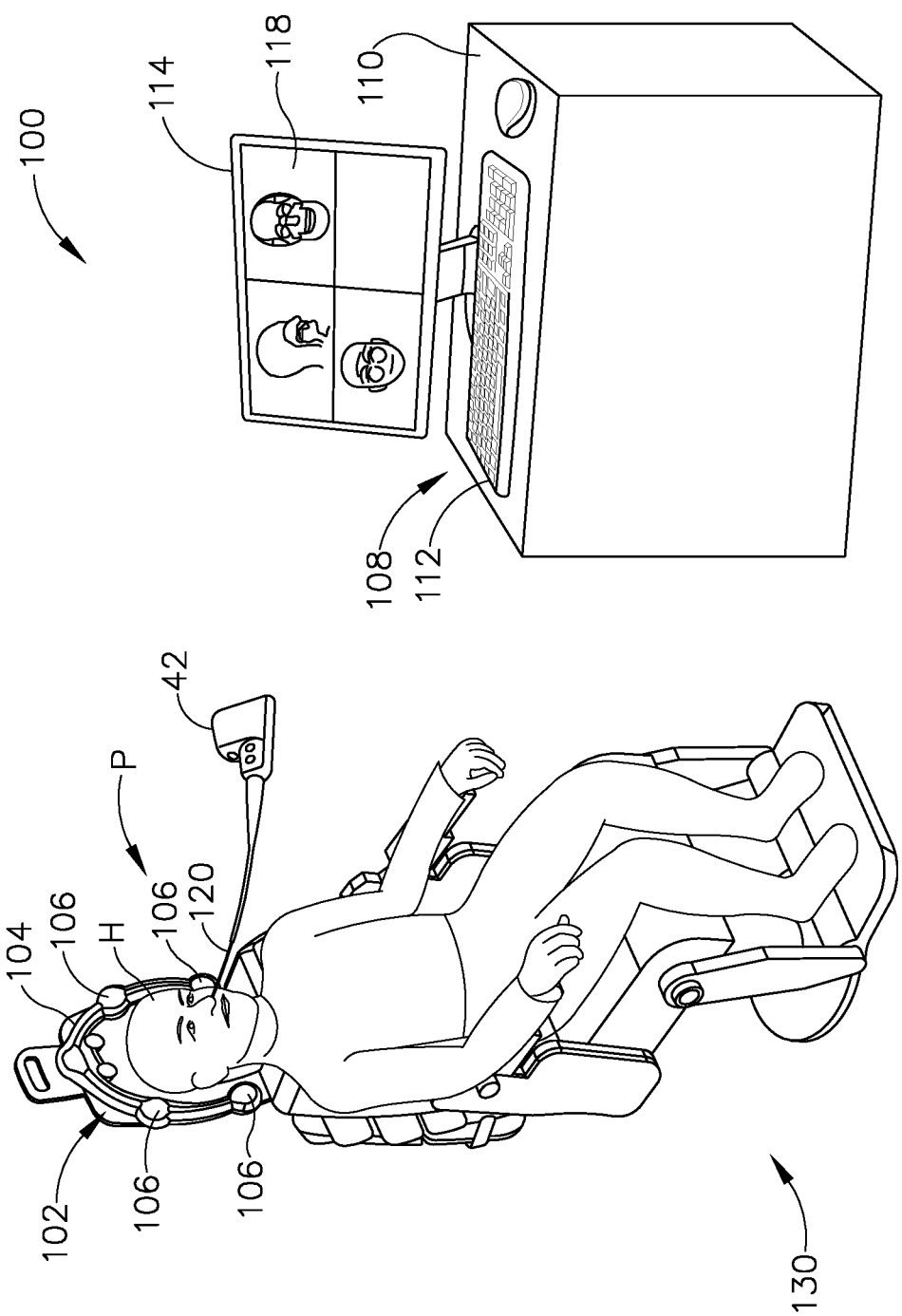
FIG. 3 depicts a schematic perspective view of an exemplary surgical navigation system.

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 3 shows an exemplary IGS navigation system (100) enabling an ENT procedure to be performed using image guidance. In addition to or in lieu of having the components and operability described herein IGS navigation system (100) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

IGS navigation system (100) of the present example comprises a field generator assembly (102), which comprises magnetic field generators (106) that are integrated into a horseshoe-shaped frame (104). Field generators (106) are operable to generate alternating magnetic fields of different frequencies around the head (H) of the patient (P). A navigation guidewire (120) is inserted into the head (H) of the patient (P) in this example. Navigation guidewire (120) may be a standalone device or may be positioned on an end effector or other location of a medical instrument such as a surgical cutting instrument or dilation instrument. In the present example, frame (104) is mounted to a chair (130), with the patient (P) being seated in the chair (130) such that frame (104) is located adjacent to the head (H) of the patient (P). By way of example only, chair (130) and/or field generator assembly (102) may be configured and operable in accordance with at least some of the teachings of U.S. patent application Ser. No. 15/933,737, entitled "Apparatus to Secure Field Generating Device to Chair," filed Mar. 23, 2018, issued as U.S. Pat. No. 10,561,370 on Feb. 18, 2020, the disclosure of which is incorporated by reference herein.

IGS navigation system (100) of the present example further comprises a processor (108), which controls field generators (106) and other elements of IGS navigation system (100). For instance, processor (108) is operable to drive field generators (106) to generate alternating electromagnetic fields; and process signals from navigation guidewire (120) to determine the location of a sensor in navigation guidewire (120) within the head (H) of the patient (P). Processor (108) comprises a processing unit communicating with one or more memories. Processor (108) of the present example is mounted in a console (110), which comprises operating controls (112) that include a keypad and/or a pointing device such as a mouse or trackball. A physician uses operating controls (112) to interact with processor (108) while performing the surgical procedure.

Navigation guidewire (120) includes a sensor (not shown) that is responsive to positioning within the alternating magnetic fields generated by field generators (106). A coupling unit (116) is secured to the proximal end of navigation guidewire (120) and is configured to provide communication of data and other signals between console (110) and navigation guidewire (120). Coupling unit (116) may provide wired or wireless communication of data and other signals between console (110) and navigation guidewire (120).

In the present example, the sensor of navigation guidewire (120) comprises at least one electrically conductive coil at the distal end of navigation guidewire (120). When such a coil is positioned within an alternating electromagnetic field generated by field generators (106), the alternating magnetic field may generate electrical current in the coil, and this electrical current may be communicated proximally along the electrical conduit(s) in navigation guidewire (120) and further to processor (108) via coupling unit (116). This phenomenon may enable IGS navigation system (100) to determine the location of the distal end of navigation guidewire (120) or other medical instrument (e.g., dilation instrument, surgical cutting instrument, etc.) within a three-dimensional space (i.e., within the head (H) of the patient (P), etc.). To accomplish this, processor (108) executes an algorithm to calculate location coordinates of the distal end of navigation guidewire (120) from the position related signals of the coil(s) in navigation guidewire (120). While the position sensor is located in guidewire (120) in this example, such a position sensor may be integrated into various other kinds of instruments, including those described in greater detail below.

Processor (108) uses software stored in a memory of processor (108) to calibrate and operate IGS navigation system (100). Such operation includes driving field generators (106), processing data from navigation guidewire (120), processing data from operating controls (112), and a driving display screen (114). In some implementations, operation may also include monitoring and enforcement of one or more safety features or functions of IGS navigation system (100). Processor (108) is further operable to provide video in real time via display screen (114), showing the position of the distal end of navigation guidewire (120) in relation to a video camera image of the patient's head (H), a CT scan image of the patient's head (H), and/or a computer generated three-dimensional model of the anatomy within and adjacent to the patient's nasal cavity. Display screen (114) may display such images (118) simultaneously and/or superimposed on each other during the surgical procedure. Such displayed images (118) may also include graphical representations of instruments that are inserted in the patient's head (H), such as navigation guidewire (120), such that the operator may view the virtual rendering of the instrument at its actual location in real time. By way of example only, display screen (114) may provide images (118) in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display screen (114).

The images (118) provided through display screen (114) may help guide the operator in maneuvering and otherwise manipulating instruments within the patient's head (H) when such instruments incorporate navigation guidewire (120). It should also be understood that other components of a surgical instrument and other kinds of surgical instruments, as described below, may incorporate a sensor like the sensor of navigation guidewire (120).

III. Exemplary Dilation Instrument With Movable Navigation Sensor

Figure 4:
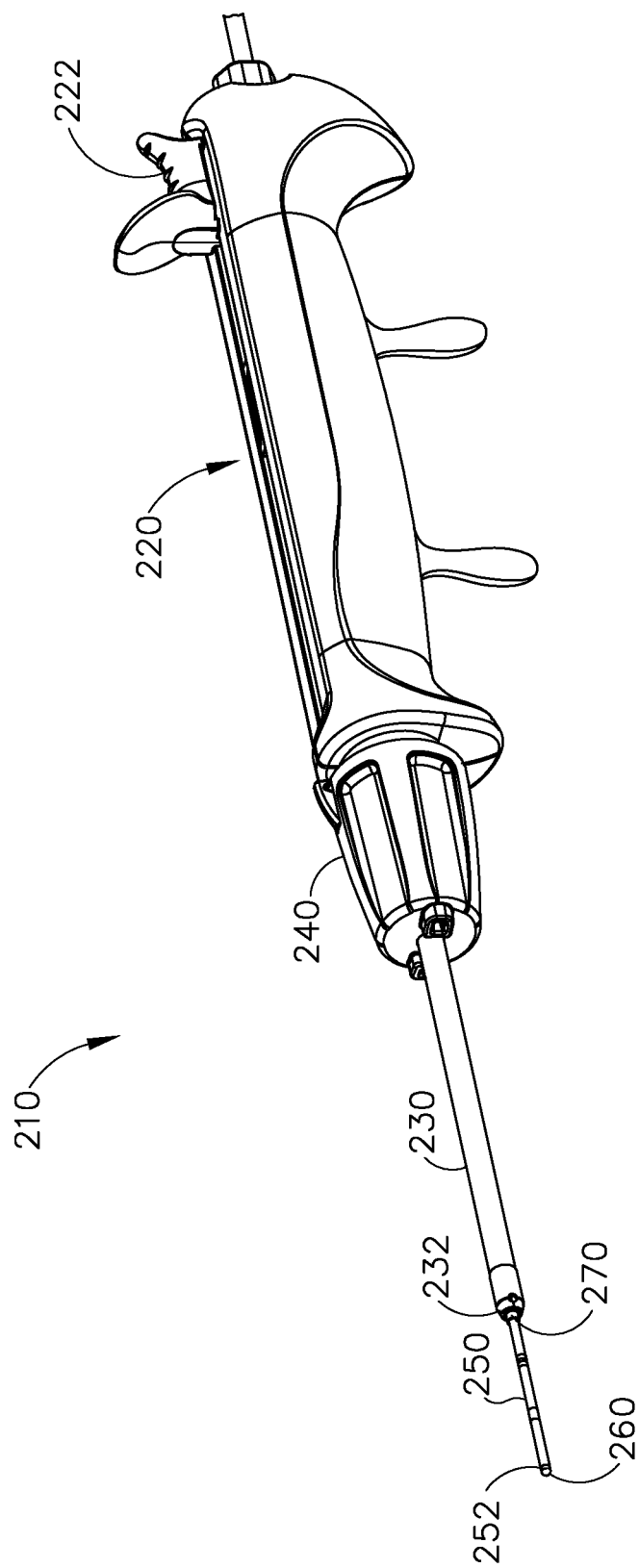
FIG. 4 depicts a perspective view of another exemplary dilation instrument, having a navigation sensor operable with the surgical navigation system of FIG. 3.

In some instances, it may be desirable to provide dilation instrument (10) with a navigation sensor operable to provide real-time tracking of a distal-most portion of dilation instrument (10) within a patient during a dilation procedure, regardless of which component of dilation instrument (10) happens to be at a distal-most position during various stages of operation of dilation instrument (10). FIG. 4 shows an exemplary alternative dilation instrument (210) having such a navigation sensor (264), which is operable with IGS navigation system (100) described above to provide real-time tracking of a distal-most portion of dilation instrument (210) within a patient (P). In particular, and as described in greater detail below, dilation instrument (210) is suitably configured such that navigation sensor (264) provides real-time tracking of both a distal end (262) of an extendable member (260) as well as a distal end (272) of a dilation catheter (270), depending on which of these components (260, 270) happens to be at a distal-most position during various stages of operation of dilation instrument (210).

A. Overview of Dilation Instrument With Movable Navigation Sensor

Dilation instrument (210) is similar in structure and function to dilation instrument (10) described above, except as otherwise described below. As shown in FIG. 4, dilation instrument (210) includes a handle assembly (220), a rigid outer guide member (230), a rotary knob (240), a malleable inner guide member (250), an extendable member (260), and a dilation catheter (270). Dilation catheter (270) is slidably disposed over malleable guide member (250), and extendable member (260) is slidably disposed within malleable guide member (250). As described in greater detail below, extendable member (260) is configured to extend and retract relative to malleable guide member (250) similar to guidewire (60) described above. However, unlike guidewire (60), extendable member (260) of this example lacks its own independently controllable slider like slider (64).

Figure 5:
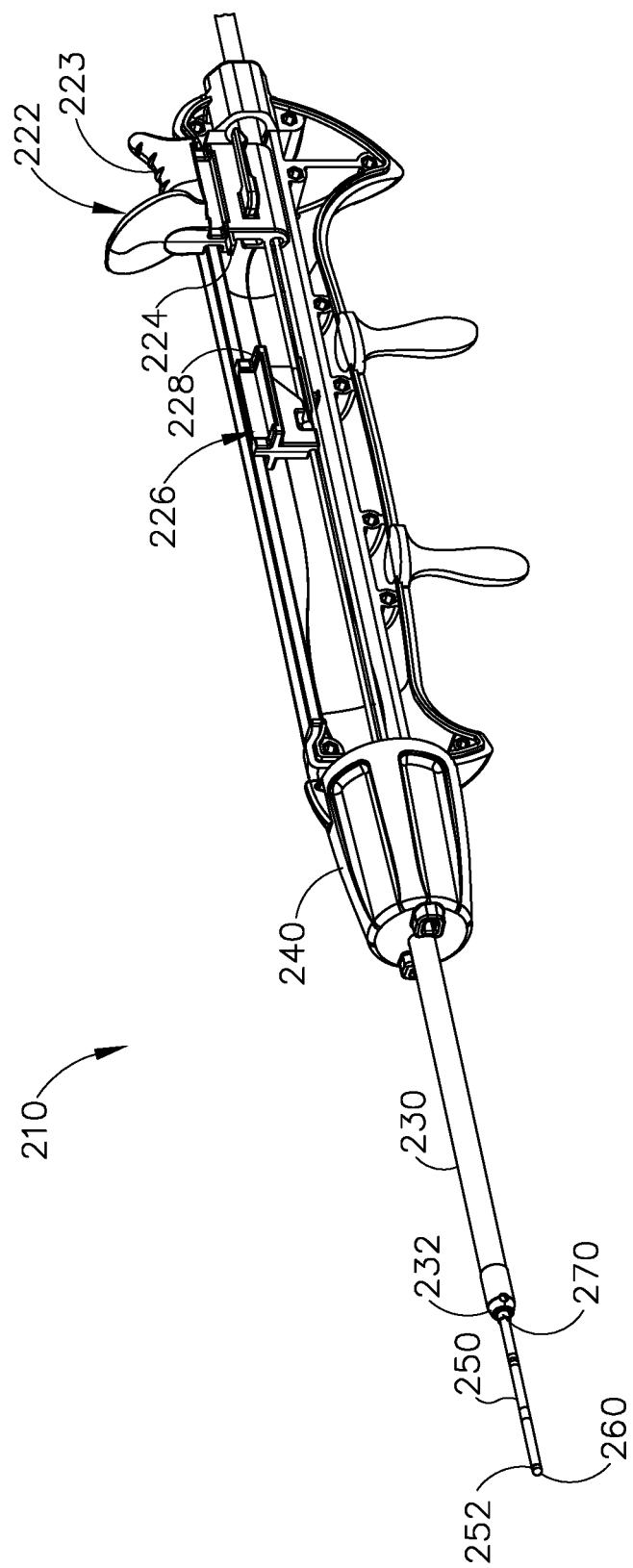
FIG. 5 depicts another perspective view of the dilation instrument of FIG. 4, with a side shroud portion of a handle assembly of the instrument omitted from view to reveal interior features of the handle assembly.
Figure 6:
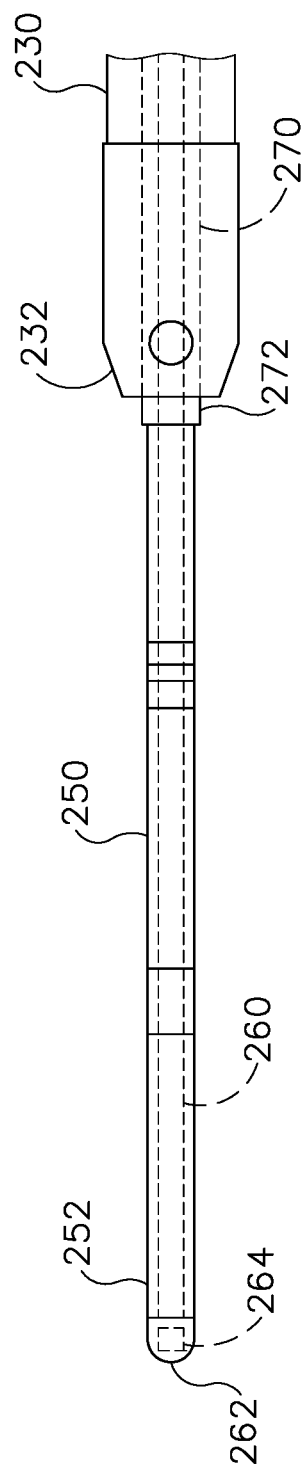
FIG. 6 depicts a schematic side elevational view of a distal portion of the dilation instrument of FIG. 4, including portions of a rigid outer guide member, a malleable inner guide member, a dilation catheter, and an extendable member having a navigation sensor in a distal tip thereof.

As shown in FIGS. 4-6, rigid guide member (230) extends distally from a distal end of handle assembly (220) and terminates at an open distal end (232). Malleable guide member (250) extends distally relative to handle assembly (220) and protrudes through open distal end (232) of rigid guide member (230), and terminates at its own open distal end (252). The outer diameter of malleable guide member (250) is smaller than the inner diameter of rigid guide member (230), such that a cylindraceous gap is defined therebetween. The cylindraceous gap is sized to permit dilation catheter (270) to translate axially therethrough, over malleable guide member (250). Similar to malleable guide member (50) described above, the distal portion of malleable guide member (250) protruding from rigid guide member (230) may be bent to a variety of desired bend angles relative to a longitudinal guide axis along which rigid guide member (230) and at least a proximal portion of malleable guide member (250) extend. Rotary knob (240) is fixedly secured to the proximal end of malleable guide member (250) and is rotatably coupled with a distal end of handle assembly (220). Similar to rotary knob (40), rotary knob (240) is configured to rotate about rigid guide member (230) and the longitudinal guide axis to thereby rotate malleable guide member (250) relative to handle assembly (220). When the distal portion of malleable guide member (250) is in a bent configuration, such rotation reorients open distal end (252) about the longitudinal guide axis As shown best in FIGS. 5 and 7A, handle assembly (220) includes a dilation catheter slider (222) and an extendable member slider (226) arranged distally of dilation catheter slider (222). Dilation catheter slider (222) is secured to a proximal portion of dilation catheter (270), such that distal and proximal movement of dilation catheter slider (222) actuates dilation catheter (270) distally and proximally over malleable guide member (250). Extendable member slider (226) is secured to a proximal portion of extendable member (260) such that distal and proximal movement of extendable member slider (226) actuates extendable member (260) distally and proximally through malleable guide member (250). In the present example, slider (226) is fully contained within handle assembly (220) such that no portion of slider (226) is exposed relative to any shroud or housing of handle assembly (220). By contrast, dilation catheter slider (222) is exposed relative to the shroud or housing of handle assembly (220), thereby enabling an operator to contact slider (222) and thereby drive slider (222) longitudinally as described in greater detail below.

The proximal portions of extendable member (260) and dilation catheter (270) may include any suitable arrangement of linking features configured to couple with the respective slider (222, 226). Sliders (222, 226) are slidably coupled with handle assembly (220) and are configured to translate distally and proximally along a longitudinal axis within an interior of handle assembly (220). Dilation catheter slider (222) of the present example includes a user-engagement feature (223) that projects upwardly through an upper longitudinal slot of handle assembly (220). User-engagement feature (223) is configured to be gripped by one or more fingers of a user to actuate dilation catheter slider (222) longitudinally.

Figure 7A:
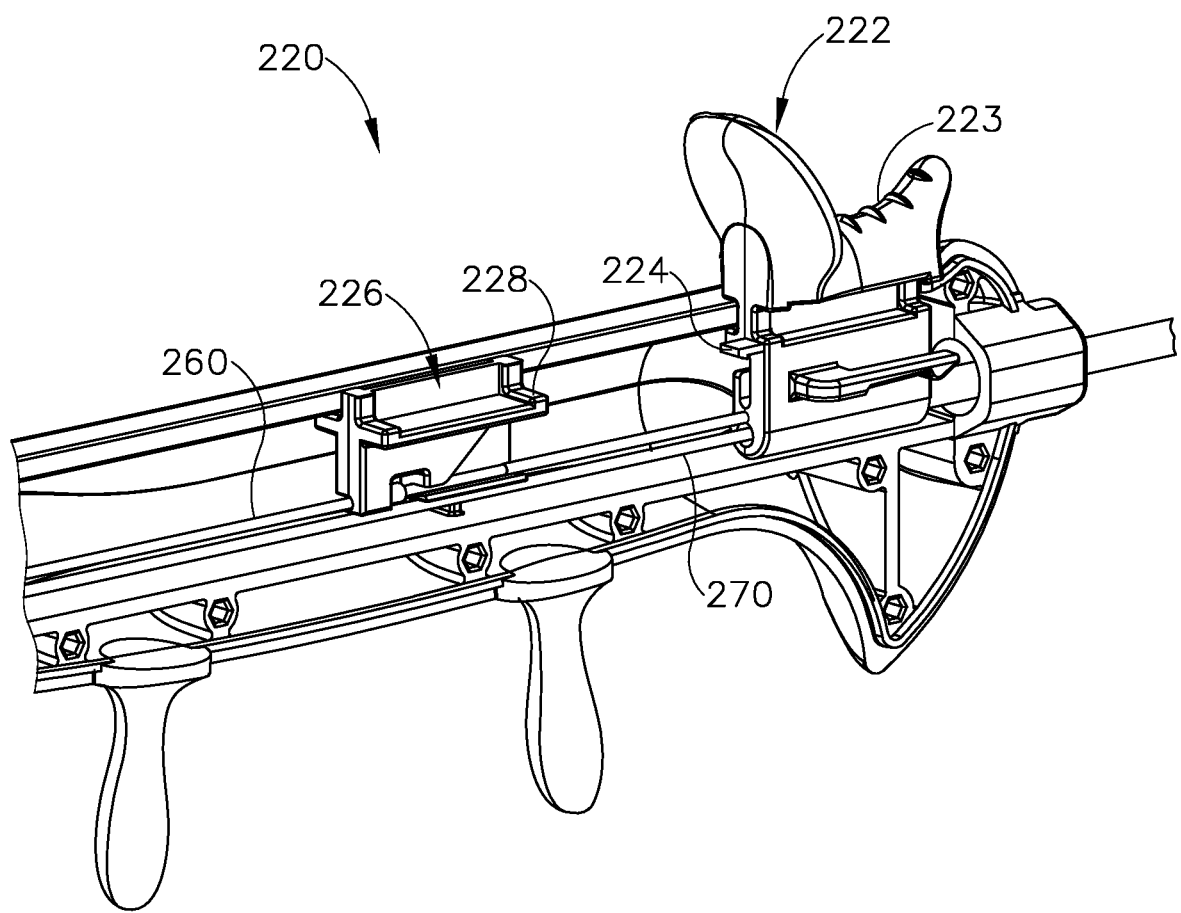
FIG. 7A depicts a perspective view of a proximal portion of the handle assembly of the dilation instrument of FIG. 4, with a side shroud portion being omitted, showing a dilation catheter slider and an extendable member slider each in proximal home positions.

As shown best in FIG. 7A, a distal end of dilation catheter slider (222) includes a first coupling feature in the form of a distally projecting latch (224). A confronting proximal end of extendable member slider (226) includes a second coupling feature in the form of an upwardly projecting ridge (228). As described in greater detail below, latch (224) is configured to capture ridge (228) and thereby releasably couple sliders (222, 226) together when dilation catheter slider (222) is driven distally into engagement with extendable member slider (226). Latch (224) is provided with a suitable degree of flexibility and resiliency to release ridge (228) and thereby permit axial separation of sliders (222, 226) when sliders (222, 226) are retracted proximally to their home positions, as described in greater detail below. In other versions, sliders (222, 226) may be provided with various other suitable types of coupling features readily apparent to those of ordinary skill in the art. For instance, sliders (222, 226) may include respective coupling features in the form of magnets.

As shown best in FIG. 6, extendable member (260) is slidably disposed within malleable guide member (250) and includes an atraumatic distal tip (262) sized to pass through a paranasal sinus ostium of a patient. Distal tip (262) of the present version is sized larger than an inner diameter of malleable guide member (250), such that distal tip (262) is configured to abut distal end (252) of malleable guide member (250) when extendable member (260) is retracted proximally by extendable member slider (226). As described below, in some versions this abutment arrests the proximal retraction of extendable member (260) and thus extendable member slider (226), thereby causing extendable member slider (226) to decouple from dilation catheter slider (222) during proximal retraction of sliders (222, 226) through handle assembly (220).

In the present example, distal tip (262) of extendable member (260) houses a navigation sensor (264) (shown schematically) operable to provide real-time tracking of distal tip (262) within patient (P) during a dilation procedure. Navigation sensor (264) of the present version is provided in the form of an electromagnetic sensor comprising one or more electrically conductive coils operable to interact with the alternating magnetic field generated by field generators (106) of surgical navigation system (100) described above. The presence of navigation sensor (264) in the alternating magnetic field induces an electrical current in the one or more coils of navigation sensor (264), which is communicated as an electrical signal proximally to coupling unit (116). In that regard, extendable member (260) may have a tubular construction defining an inner lumen through which one or more sensor wires (not shown) extends to electrically couple navigation sensor (264) with coupling unit (116). Electrical signals generated by navigation sensor (264) may be communicated through the sensor wires to coupling unit (116). Coupling unit (116) then transmits the electrical signals to processor (108) mounted in console (110) (see FIG. 3).

In response to receiving signals from coupling unit (116), processor (108) executes an algorithm to determine a location of navigation sensor (264) within a three-dimensional space occupied by the alternating magnetic field produced by field generators (106). Processor (108) correlates this three-dimensional space to the known anatomy of patient (P), analyzed preoperatively, and determines the three-dimensional location of navigation sensor (264) within patient (P). Because navigation sensor (264) is housed within distal tip (262) of extendable member (260) in the present example, this determined 3-dimensional location of navigation sensor (264) thus corresponds to a location of distal tip (262) within patient (P). Processor (108) may then drive display screen (114) to provide a visual indication of the position of distal tip (262), in real time, on one or more preoperatively obtained images of the patient's head (H), as described above and as described in various references cited herein.

B. Exemplary Actuation of Dilation Instrument Features

FIGS. 7A-7E and 8A-8E show exemplary operation of dilation catheter slider (222) to effect distal extension and proximal retraction of dilation catheter (270) and extendable member (260) relative to handle assembly (220). As described above, dilation catheter slider (222) is configured to releasably couple with extendable member slider (226) such that dilation catheter slider (222) is engageable by a user to actuate both dilation catheter (270) and extendable member (260) longitudinally relative to malleable guide member (250). Accordingly, as described in greater detail below, dilation catheter slider (222) is configured to provide joint actuation of dilation catheter (270) and extendable member (260) through a predetermined range of longitudinal motion. In other versions, extendable member slider (226) may also include a user-engagement feature that enables extendable member slider (226) to be actuated by a user independently of dilation catheter slider (222).

Figure 8A:
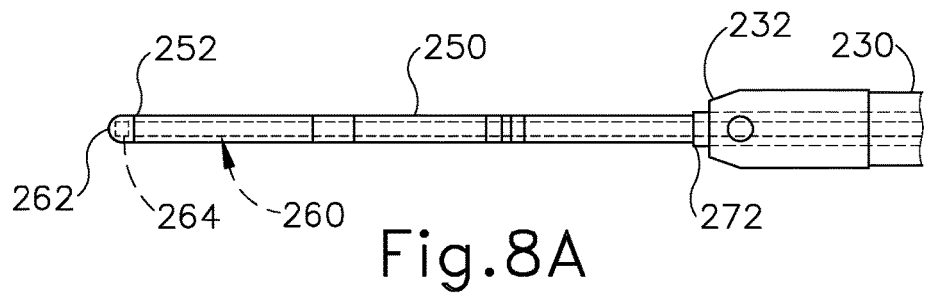
FIG. 8A depicts a schematic side elevational view of a distal portion of the dilation instrument of FIG. 4, showing the dilation catheter and the extendable member in respective proximal positions when the dilation catheter slider and the extendable member slider are in the respective proximal home positions of FIG. 7A.

FIG. 7A shows dilation catheter slider (222) and extendable member slider (226) in respective proximal home positions within handle assembly (220). Dilation catheter slider (222) is positioned at a proximal end of handle assembly (220), and extendable member slider (226) is positioned at a medial portion of handle assembly (220) spaced distally from dilation catheter slider (222). As shown in FIG. 8A, these proximal home positions of sliders (222, 226) position a distal end (272) of dilation catheter (270) at distal end (232) of rigid guide member (230), and distal tip (262) of extendable member (260) at distal end (252) of malleable guide member (250). Accordingly, in the configuration of FIGS. 7A and 8A, the signals generated by navigation sensor (264) correspond to a location of only distal tip (262) of extendable member (260) and distal end (252) of malleable guide member (250) within patient (P). The operator may rely on the position feedback from navigation sensor (264) and IGS navigation system (100) in order to maneuver dilation instrument (210) such that distal end (252) is positioned at or near a targeted anatomical passageway (e.g., paranasal sinus ostium, frontal recess, Eustachian tube, etc.) in the head (H) of the patient (P).

Figure 7B:
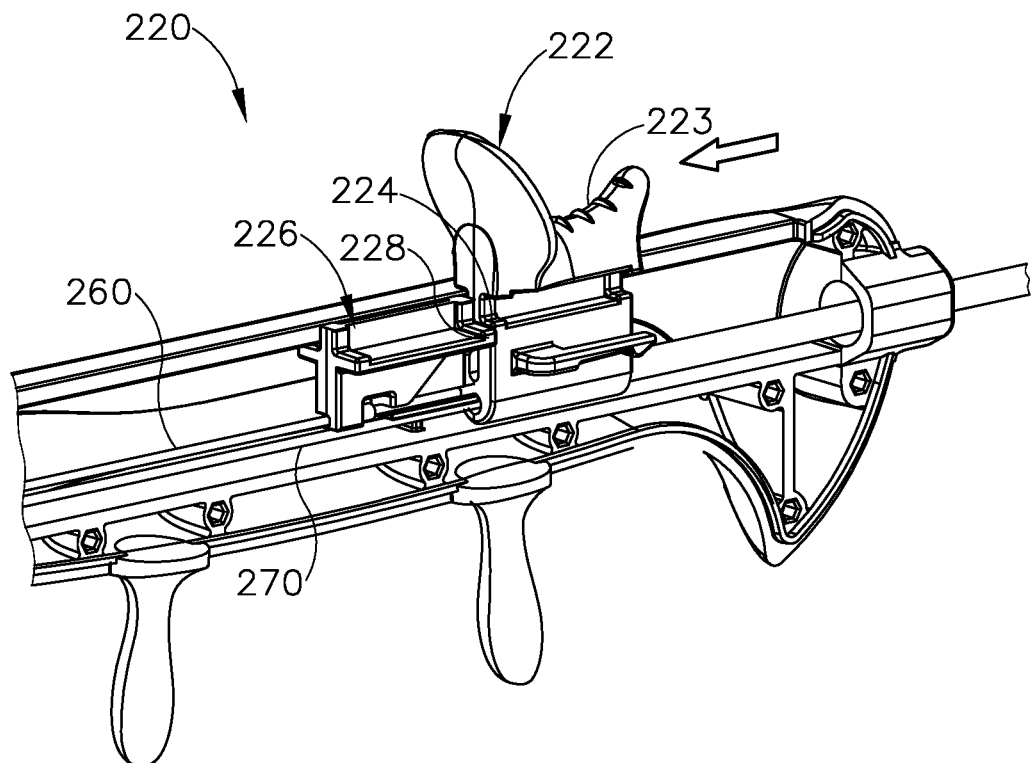
FIG. 7B depicts another perspective view of the proximal portion of the handle assembly of FIG. 7A, showing the dilation catheter slider after having advanced distally through a first range of motion so that the dilation catheter slider couples with the extendable member slider.
Figure 8B:
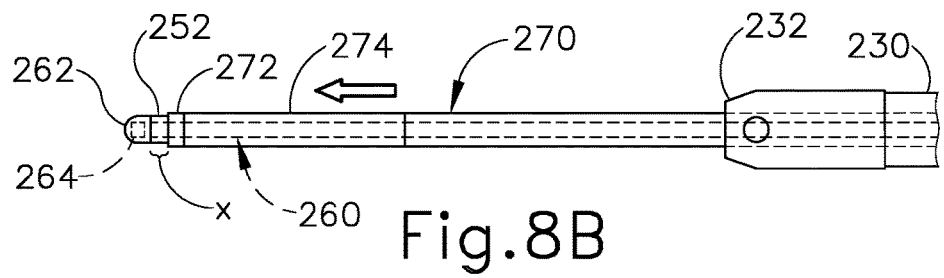
FIG. 8B depicts another schematic side elevational view of the distal portion of the dilation instrument of FIG. 4, showing the dilation catheter and the extendable member in respective positions when the dilation catheter slider and the extendable member slider are in the respective positions of FIG. 7B.

Once the operator has achieved the desired position of distal end (252) at or near a targeted anatomical passageway (e.g., paranasal sinus ostium, frontal recess, Eustachian tube, etc.) in the head (H) of the patient (P) by relying on position feedback from navigation sensor (264) and IGS navigation system (100), the operator may then actuate dilation catheter slider (222) in order to position a dilator (274) of dilation catheter (270) in the targeted anatomical passageway. As shown in FIGS. 7B and 8B, dilation catheter slider (222) and dilation catheter (270) are advanced distally through a first range of motion relative to handle assembly (220) and malleable guide member (250) while extendable member slider (226) and extendable member (260) remain stationary. Upon reaching the distal end of this first range of motion, distal latch (224) of dilation catheter slider (222) resiliently engages proximal ridge (228) of extendable member slider (226), thereby releasably coupling sliders (222, 226) together. Extendable member slider (226) may include a detent feature configured to provide a proximally directed force (i.e., mechanical resistance) suitable to facilitate full engagement of distal latch (224) with proximal ridge (228).

As shown in FIG. 8B, distal end (272) of dilation catheter (270) is advanced to a position at or near distal end (252) of malleable guide member (250) upon reaching the distal end of the first range of motion. Once extended through the first range of motion in the present example, distal end (272) of dilation catheter (270) is spaced proximally from distal tip (262) of extendable member (260) by a predetermined longitudinal spacing (X). In versions where longitudinal spacing (X) is nominal, such as in the present example, the signals generated by navigation sensor (264) may be interpreted to correspond to a location of both distal tip (262) of extendable member (260) and distal end (272) of dilation catheter (270) within patient (P). In versions where longitudinal spacing (X) is greater than nominal, a location of dilation catheter distal end (272) within patient (P) may be calculated by processor (108) based on the sensed location of extendable member distal tip (262) and a known magnitude of longitudinal spacing (X). It will be appreciated that longitudinal spacing (X) may be adjusted as desired by modifying a length and/or the proximal home position of extendable member slider (226) and/or dilation catheter slider (222). In some versions, sliders (222, 226) and dilation catheter (270) may be suitably configured such that dilation catheter distal end (272) is substantially flush with a distal-most point of extendable member distal tip (262) when dilation catheter slider (222) has been advanced fully through the first range of motion, such that longitudinal spacing (X) is approximately zero.

Figure 7C:
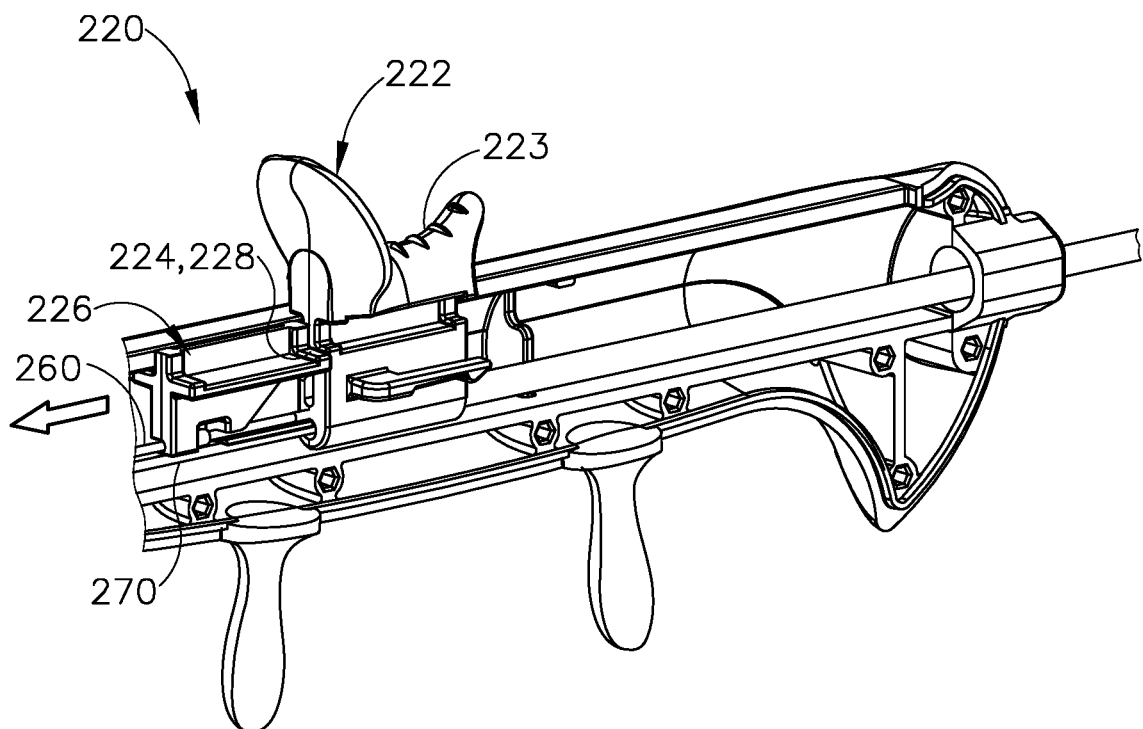
FIG. 7C depicts another perspective view of the proximal portion of the handle assembly of FIG. 7A, showing the dilation catheter slider and the extendable member slider after having advanced distally together through a second range of motion.
Figure 8C:
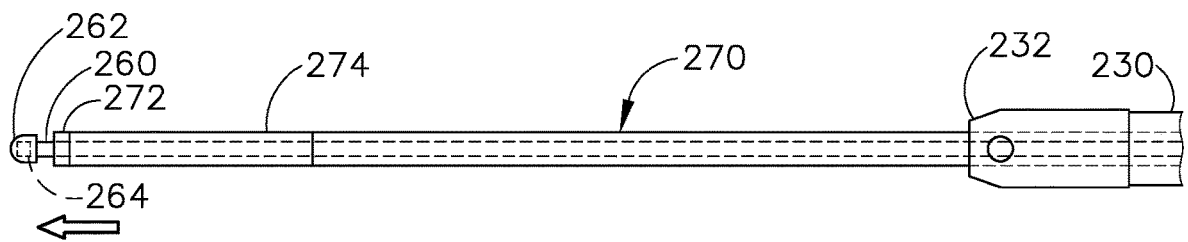
FIG. 8C depicts another schematic side elevational view of the distal portion of the dilation instrument of FIG. 4, showing the dilation catheter and the extendable member in respective positions when the dilation catheter slider and the extendable member slider are in the respective positions of FIG. 7C.

As shown in FIGS. 7C and 8C, continued distal advancement of dilation catheter slider (222) via user-engagement feature (223) drives extendable member slider (226) distally as well, such that both sliders (222, 226), dilation catheter (270), and extendable member (260) translate jointly through a second range of motion that is distal to the first range of motion shown in FIGS. 7A-7B and 8A-8B. While translating through this second range of motion, the signals generated by navigation sensor (264) correspond to a location within patient (P) of both extendable member distal tip (262) and dilation catheter distal end (272), due to the nominal magnitude of longitudinal spacing (X) (or otherwise known and fixed spacing (X)) described above.

The operator may again rely on the position feedback from navigation sensor (264) and IGS navigation system (100) in order to determine whether dilation catheter distal end (272) has successfully entered into the targeted anatomical passageway (e.g., paranasal sinus ostium, frontal recess, Eustachian tube, etc.) during the second range of motion. Moreover, since the distance between distal end (272) and dilator (274) is known and fixed, the operator may rely on the position feedback from navigation sensor (264) and IGS navigation system (100) in order to determine whether dilator (274) has successfully entered into the targeted anatomical passageway during the second range of motion. Upon confirming that dilator (274) has successfully entered into the targeted anatomical passageway, the operator may deem the second range of motion complete.

Upon reaching a distal end of the second range of motion, which corresponds to a desired positioning of dilator (274) in the targeted anatomical passageway, dilator (274) of dilation catheter (270) may be positioned in the targeted anatomical passageway and expanded to thereby dilate the anatomical passageway of patient (P) in which dilator (274) is positioned. Similar to dilator (72) described above, dilator (274) may be in the form of an inflatable balloon or a variety of other selectively expandable members readily apparent to those of ordinary skill in the art in view of the teachings herein. Following dilation of the anatomical passageway, and any additional treatment steps, dilator (274) may be contracted (e.g., deflated).

Figure 7D:
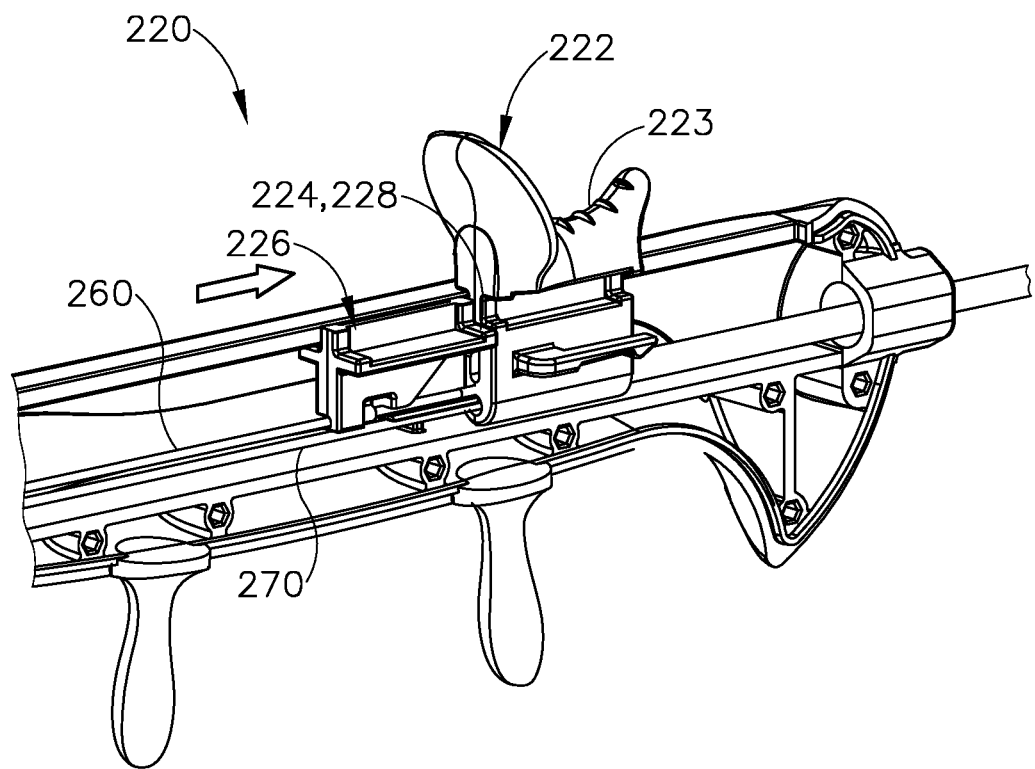
FIG. 7D depicts another perspective view of the proximal portion of the handle assembly of FIG. 7A, showing the dilation catheter slider and the extendable member slider after having retracted proximally together through the second range of motion such that the extendable member slider returns to its proximal home position.
Figure 8D:
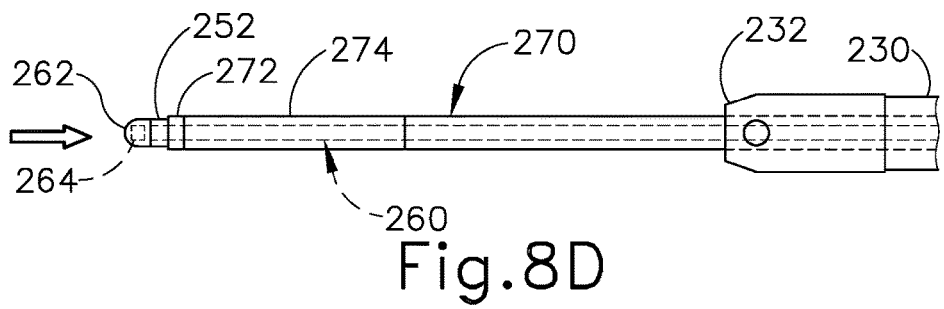
FIG. 8D depicts another schematic side elevational view of the distal portion of the dilation instrument of FIG. 4, showing the dilation catheter and the extendable member in respective positions when the dilation catheter slider and the extendable member slider are in the respective positions of FIG. 7D.

As shown in FIGS. 7D and 8D, dilation catheter slider (222) may then be actuated proximally to thereby retract extendable member slider (226), extendable member (260), and dilation catheter (270) proximally through the second range of motion. In that regard, sliders (222, 226) remain coupled together throughout proximal retraction through the second range of motion via engagement of distal latch (224) with proximal ridge (228). Accordingly, throughout the second range of motion, proximal actuation of dilation catheter slider (222) effects proximal actuation of extendable member slider (226) and thus extendable member (260). As shown in FIG. 7D, extendable member slider (226) reassumes its proximal home position upon retracting to the proximal end of the second range of motion.

Figure 7E:
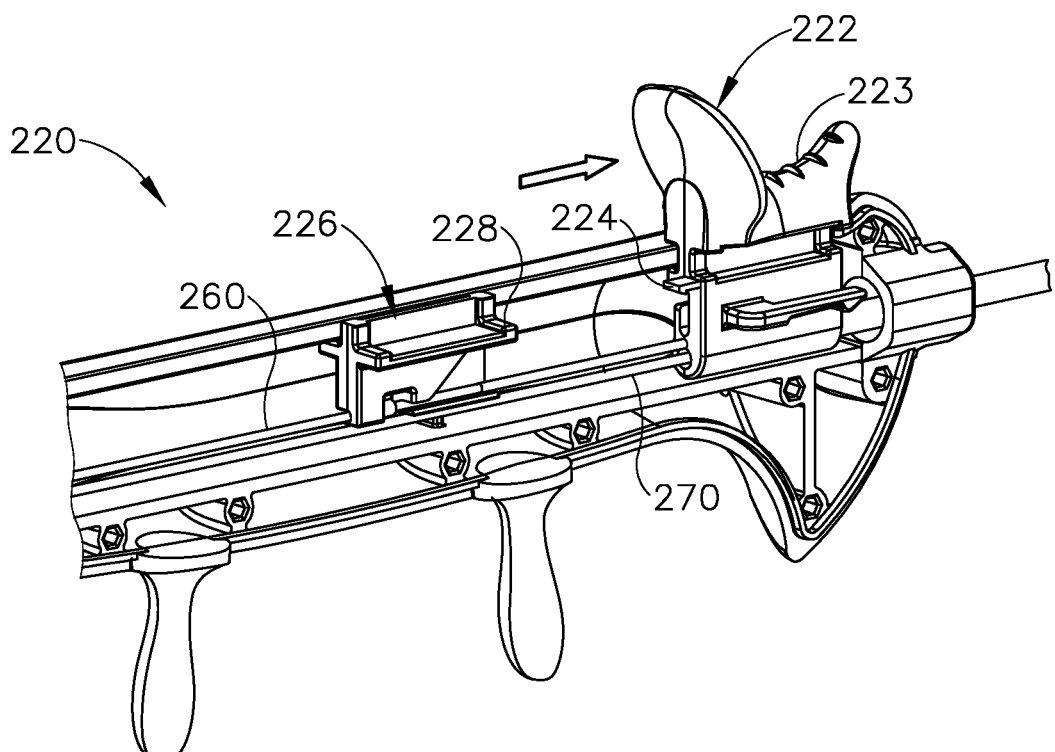
FIG. 7E depicts another perspective view of the proximal portion of the handle assembly of FIG. 7A, showing the dilation catheter slider and the extendable member slider having decoupled so that the dilation catheter slider retracts proximally through the first range of motion to its proximal home position while the extendable member slider remains in its proximal home position.
Figure 8E:
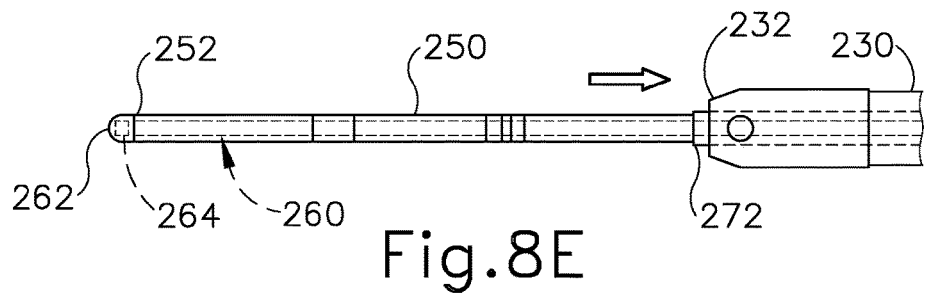
FIG. 8E depicts another schematic side elevational view of the distal portion of the dilation instrument of FIG. 4, showing the dilation catheter and the extendable member in respective positions when the dilation catheter slider and the extendable member slider are in the respective positions of FIG. 7E.

As shown in FIG. 7E, continued proximal retraction of dilation catheter slider (222) from the second range of motion into the first range of motion causes sliders (222, 226) to decouple from one another, via disengagement of distal latch (224) from proximal ridge (228), such that extendable member slider (226) remains in its proximal home position. In the present example, this decoupling of sliders (222, 226) is provided by abutting engagement of distal tip (262) of extendable member (260) with distal end (252) of malleable guide member (250), due to the outer diameter of distal tip (262) being larger than the inner diameter of distal end (252), as described above. In other versions, distal tip (262) may be provided with any suitable size (e.g., smaller than distal end (252)), and the decoupling of sliders (222, 226) may be provided by features incorporated within handle assembly (220). For instance, upon being retracted to its proximal home position, extendable member slider (226) may be configured to engage a projection (e.g., a boss) or other suitable feature provided in the interior of handle assembly (220) that prevents further proximal retraction of extendable member slider (226) and extendable member (260). In either case, as shown in FIG. 8E, distal tip (262) of extendable member (260) remains stationary at distal end (252) of malleable guide member (250) while distal end (272) of dilation catheter (270) retracts further proximally to distal end (232) of rigid guide member (230).

As described above, navigation sensor (264) is configured to enable surgical navigation system (100) to track a location of extendable member distal tip (262) within patient (P) during a dilation procedure. Because dilation catheter (270) and extendable member (260) are configured to extend and retract jointly through a second range of motion in which dilation catheter distal end (272) and extendable member distal tip (262) are separated by a nominal longitudinal spacing (X), the signals generated by navigation sensor (264) throughout the second range of motion correspond to a location of both distal tip (262) and distal end (272) within patient (P). Accordingly, and advantageously, navigation sensor (264) enables a user of dilation instrument (210) to effectively monitor the location of distal tip (262) and distal end (272) within patient (P) via a single navigation sensor (264). Of course, it will be appreciated that in other versions one or more additional navigation sensors (264) may be provided to independently track the location of other portions of dilation instrument (210) relative to patient (P) during a dilation procedure.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus comprising: (a) a handle assembly; (b) a guide member extending distally from the handle assembly; (c) a dilation catheter slidably disposed relative to the guide member, wherein the dilation catheter includes an expandable element configured to dilate a paranasal sinus ostium of a patient; and (d) a navigation sensor movably disposed at the distal end of the guide member, wherein the navigation sensor is operable to generate a signal corresponding to a location thereof within the patient, wherein the navigation sensor is configured to translate distally with the dilation catheter relative to the guide member when a distal end of the dilation catheter translates distally beyond the distal end of the guide member, wherein the navigation sensor is configured to assume a position at the distal end of the guide member when the distal end of the dilation catheter retracts proximally of the distal end of the guide member.

EXAMPLE 2

The apparatus of Example 1, further comprising an extendable member slidably disposed within the guide member, wherein the extendable member is configured to extend and retract relative to the guide member and the handle assembly, wherein a distal end of the extendable member is sized to pass through a paranasal sinus ostium of a patient.

EXAMPLE 3

The apparatus of Example 2, wherein the distal end of the extendable member is configured to stop at a distal end of the guide member in response to proximal retraction of the dilation catheter relative to the handle assembly.

EXAMPLE 4

The apparatus of any of Examples 2 through 3, wherein the distal end of the extendable member is configured to abut the distal end of the guide member in response to proximal retraction of the dilation catheter relative to the handle assembly.

EXAMPLE 5

The apparatus of any of Examples 2 through 4, wherein the handle assembly comprises: (a) a first slidable member operatively coupled with the dilation catheter, wherein the first slidable member is operable to actuate the dilation catheter relative to the handle assembly, and (b) a second slidable member operatively coupled with the extendable member, wherein the second slidable member is operable to actuate the extendable member relative to the handle assembly.

EXAMPLE 6

The apparatus of Example 5, wherein the first slidable member is positioned proximal to the second slidable member.

EXAMPLE 7

The apparatus of any of Examples 5 through 6, wherein the first slidable member is translatable through a first range of motion independently of the second slidable member, wherein the first slidable member is translatable through a second range of motion jointly with the second slidable member, wherein the second range of motion is distal to the first range of motion.

EXAMPLE 8

The apparatus of Example 7, wherein the first slidable member is operable to drive the second slidable member through the second range of motion.

EXAMPLE 9

The apparatus of any of Examples 7 through 8, wherein the first slidable member includes a user-engagement feature configured to be engaged by a user for actuating both the first slidable member and the second slidable member through the second range of motion.

EXAMPLE 10

The apparatus of any of Examples 7 through 9, wherein at least one of the first slidable member or the second slidable member includes a coupling feature configured to releasably couple with the other of the first slidable member or the second slidable member in response to distal actuation of the first slidable member from the first range of motion into the second range of motion.

EXAMPLE 11

The apparatus of Example 10, wherein the coupling feature is configured to disengage the other of the first slidable member or the second slidable member in response to proximal retraction of the first slidable member from the second range of motion into the first range of motion.

EXAMPLE 12

The apparatus of any of Examples 10 through 11, wherein the coupling feature comprises at least one of a latch or a magnet.

EXAMPLE 13

The apparatus of any of the preceding Examples, wherein the navigation sensor comprises an electromagnetic sensor.

EXAMPLE 14

The apparatus of any of the preceding Examples, wherein at least a distal portion of the guide member is malleable and configured to assume a bent configuration relative to a longitudinal axis of a proximal portion of the guide member,

EXAMPLE 15

The apparatus of any of the preceding Examples, wherein the guide member comprises a first guide member, wherein the apparatus further comprises a second guide member extending distally from the handle assembly and disposed around at least a proximal portion of the first guide member to define a cylindraceous gap therebetween, wherein the dilation catheter is configured to translate through the cylindraceous gap.

EXAMPLE 16

An apparatus comprising: (a) a handle assembly; (b) an extendable member configured to extend and retract relative to the handle assembly, wherein a distal end of the extendable member is sized to pass through a paranasal sinus ostium of a patient; (c) a navigation sensor secured to the distal end of the extendable member, wherein the navigation sensor is operable to generate a signal corresponding to a location thereof within the patient; and (d) a dilation catheter slidably disposed about the extendable member, wherein the dilation catheter includes an expandable member operable to dilate the paranasal sinus ostium, wherein the dilation catheter is configured to translate through a first range of motion independently of the extendable member, such that the signal generated by the navigation sensor throughout the first range of motion corresponds to a location of the distal end of the extendable member within the patient, wherein the dilation catheter and the extendable member are configured to translate jointly through a second range of motion distal to the first range of motion, such that the signal generated by the navigation sensor throughout the second range of motion corresponds to a location of a portion of the dilation catheter within the patient.

EXAMPLE 17

The apparatus of Example 16, wherein the extendable member is configured to translate distally through the second range of motion with the dilation catheter in response to distal actuation of the dilation catheter through a distal end of the first range of motion.

EXAMPLE 18

The apparatus of any of Examples 16 through 17, wherein the signal generated by the navigation sensor throughout the second range of motion corresponds to a location of a distal end of the dilation catheter within the patient.

EXAMPLE 19

The apparatus of any of Examples 16 through 18, further comprising a guide member extending distally from the handle assembly, wherein the dilation catheter is slidably disposed over the guide member, wherein the distal end of the extendable member is configured to remain stationary at a distal end of the guide member while the dilation catheter translates over the guide member through the first range of motion.

EXAMPLE 20

An apparatus comprising: (a) a handle assembly; (b) a guide member extending distally from the handle assembly;

(c) an extendable member slidably disposed within the guide member, wherein the extendable member is configured to extend and retract relative to the guide member and the handle assembly, wherein a distal end of the extendable member is sized to pass through a paranasal sinus ostium of a patient; (d) a navigation sensor secured to the distal end of the extendable member, wherein the navigation sensor is operable to generate a signal corresponding to a location of the distal end of the extendable member within the patient; and (e) a dilation catheter slidably disposed relative to the guide member, wherein the dilation catheter includes an expandable member operable to dilate the paranasal sinus ostium.

V. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
(a) a handle assembly;
(b) a guide member extending distally from the handle assembly;
(c) a dilation catheter slidably disposed relative to the guide member, wherein the dilation catheter includes an expandable element configured to dilate a paranasal sinus ostium of a patient; and
(d) a navigation sensor movable from a position at the distal end of the guide member, wherein the navigation sensor is operable to generate a signal corresponding to a location thereof within the patient,
wherein the navigation sensor is configured to translate distally with the dilation catheter relative to the guide member in response to a distal end of the dilation catheter translating distally beyond the distal end of the guide member,
wherein the navigation sensor is configured to assume the position at the distal end of the guide member in response to the distal end of the dilation catheter retracting proximally of the distal end of the guide member.

2. The apparatus of claim 1, further comprising an extendable member slidably disposed within the guide member, wherein the extendable member is configured to extend and retract relative to the guide member and the handle assembly, wherein a distal end of the extendable member is sized to pass through a paranasal sinus ostium of a patient.

3. The apparatus of claim 2, wherein the distal end of the extendable member is configured to stop at the distal end of the guide member in response to proximal retraction of the dilation catheter relative to the handle assembly.

4. The apparatus of claim 2, wherein the distal end of the extendable member is configured to abut the distal end of the guide member in response to proximal retraction of the dilation catheter relative to the handle assembly.

5. The apparatus of claim 2, wherein the handle assembly comprises:
(a) a first slidable member operatively coupled with the dilation catheter, wherein the first slidable member is operable to actuate the dilation catheter relative to the handle assembly, and
(b) a second slidable member operatively coupled with the extendable member, wherein the second slidable member is operable to actuate the extendable member relative to the handle assembly.

6. The apparatus of claim 5, wherein the first slidable member is positioned proximal to the second slidable member.

7. The apparatus of claim 5, wherein the first slidable member is translatable through a first range of motion independently of the second slidable member, wherein the first slidable member is translatable through a second range of motion jointly with the second slidable member, wherein the second range of motion is distal to the first range of motion.

8. The apparatus of claim 7, wherein the first slidable member is operable to drive the second slidable member through the second range of motion.

9. The apparatus of claim 7, wherein the first slidable member includes a user-engagement feature configured to be engaged by a user for actuating both the first slidable member and the second slidable member through the second range of motion.

10. The apparatus of any of claim 7, wherein at least one of the first slidable member or the second slidable member includes a coupling feature configured to releasably couple with the other of the first slidable member or the second slidable member in response to distal actuation of the first slidable member from the first range of motion into the second range of motion.

11. The apparatus of claim 10, wherein the coupling feature is configured to disengage the other of the first slidable member or the second slidable member in response to proximal retraction of the first slidable member from the second range of motion into the first range of motion.

12. The apparatus of any of claim 10, wherein the coupling feature comprises at least one of a latch or a magnet.

13. The apparatus of claim 1, wherein the navigation sensor comprises an electromagnetic sensor.

14. The apparatus of claim 1, wherein at least a distal portion of the guide member is malleable and configured to assume a bent configuration relative to a longitudinal axis of a proximal portion of the guide member.

15. The apparatus of claim 1, wherein the guide member comprises a first guide member, wherein the apparatus further comprises a second guide member extending distally from the handle assembly and disposed around at least a proximal portion of the first guide member to define a cylindraceous gap therebetween, wherein the dilation catheter is configured to translate through the cylindraceous gap.

16. An apparatus comprising:
(a) a handle assembly;
(b) an extendable member configured to extend and retract relative to the handle assembly, wherein a distal end of the extendable member is sized to pass through a paranasal sinus ostium of a patient;
(c) a navigation sensor secured to the distal end of the extendable member, wherein the navigation sensor is operable to generate a signal corresponding to a location thereof within the patient; and
(d) a dilation catheter slidably disposed about the extendable member, wherein the dilation catheter includes an expandable member operable to dilate the paranasal sinus ostium,
wherein the dilation catheter is configured to translate through a first range of motion independently of the extendable member, such that the signal generated by the navigation sensor throughout the first range of motion corresponds to a location of the distal end of the extendable member within the patient,
wherein the dilation catheter and the extendable member are configured to translate jointly through a second range of motion distal to the first range of motion, such that the signal generated by the navigation sensor throughout the second range of motion corresponds to a location of a portion of the dilation catheter within the patient.

17. The apparatus of claim 16, wherein the extendable member is configured to translate distally through the second range of motion with the dilation catheter in response to distal actuation of the dilation catheter through a distal end of the first range of motion.

18. The apparatus of claim 16, wherein the signal generated by the navigation sensor throughout the second range of motion corresponds to a location of a distal end of the dilation catheter within the patient.

19. The apparatus of claim 16, further comprising a guide member extending distally from the handle assembly, wherein the dilation catheter is slidably disposed over the guide member, wherein the distal end of the extendable member is configured to remain stationary at a distal end of the guide member while the dilation catheter translates over the guide member through the first range of motion.

20. An apparatus comprising:
(a) a handle assembly;
(b) a guide member extending distally from the handle assembly;
(c) an extendable member slidably disposed within the guide member, wherein the extendable member is configured to extend and retract relative to the guide member and the handle assembly, wherein a distal end of the extendable member is sized to pass through a paranasal sinus ostium of a patient;
(d) a navigation sensor secured to the distal end of the extendable member, wherein the navigation sensor is operable to generate a signal corresponding to a location of the distal end of the extendable member within the patient; and
(e) a dilation catheter slidably disposed relative to the guide member, wherein the dilation catheter includes an expandable member operable to dilate the paranasal sinus ostium.

* * * * *